(12) United States Patent
Kaplan et al.

(10) Patent No.: US 8,195,021 B2
(45) Date of Patent: Jun. 5, 2012

(54) BIOPOLYMER OPTICAL WAVEGUIDE AND METHOD OF MANUFACTURING THE SAME

(75) Inventors: David L. Kaplan, Concord, MA (US); Fiorenzo Omenetto, Wakefield, MA (US); Brian Lawrence, New York, NY (US); Mark Cronin-Golomb, Reading, MA (US)

(73) Assignee: Tufts University/Trustees of Tufts College, Medford, MA (US)

( * ) Notice: Subject to any disclaimer, the term of this patent is extended or adjusted under 35 U.S.C. 154(b) by 262 days.

(21) Appl. No.: 12/513,387

(22) PCT Filed: Nov. 5, 2007

(86) PCT No.: PCT/US2007/083605
§ 371 (c)(1),
(2), (4) Date: May 4, 2009

(87) PCT Pub. No.: WO2008/127401
PCT Pub. Date: Oct. 23, 2008

(65) Prior Publication Data
US 2010/0063404 A1      Mar. 11, 2010

Related U.S. Application Data

(60) Provisional application No. 60/856,297, filed on Nov. 3, 2006.

(51) Int. Cl.
G02B 6/10 (2006.01)
G02B 1/12 (2006.01)
A61N 5/06 (2006.01)
A61B 6/00 (2006.01)

(52) U.S. Cl. ............... 385/131; 385/12; 385/33; 385/37; 385/14; 600/478; 264/1.24; 264/1.27; 607/92

(58) Field of Classification Search ............ 385/12, 385/129, 130, 131, 132, 141, 142, 33, 37, 385/14; 264/1.24, 1.27; 607/92; 600/478
See application file for complete search history.

(56) References Cited

U.S. PATENT DOCUMENTS

| | | | | |
|---|---|---|---|---|
| 5,512,218 A * | 4/1996 | Gresser et al. | ............... | 264/1.34 |
| 6,134,045 A * | 10/2000 | Jiang et al. | ............... | 359/321 |
| 6,284,418 B1 * | 9/2001 | Trantolo | ............... | 430/20 |
| 7,223,609 B2 * | 5/2007 | Anvar et al. | ............... | 436/165 |
| 2001/0003043 A1 * | 6/2001 | Metspalu et al. | ............... | 435/6 |
| 2004/0081384 A1 * | 4/2004 | Datesman et al. | ............... | 385/12 |

(Continued)

FOREIGN PATENT DOCUMENTS
JP      01 280242 A      11/1989
(Continued)

*Primary Examiner* — Brian Healy
(74) *Attorney, Agent, or Firm* — Choate Hall & Stewart LLP (57) ABSTRACT

A method of manufacturing a biopolymer optical waveguide includes providing a biopolymer, unwinding the biopolymer progressively to extract individual biopolymer fibers, and putting the unwound fibers under tension. The tensioned fibers are then cast in a different polymer to form a biopolymer optical waveguide that guides light due to the difference in indices of refraction between the biopolymer and the different polymer. The optical fibers may be used in biomedical applications and can be inserted in the body as transmissive media. Printing techniques may be used to manufacture the biopolymer optical waveguides.

27 Claims, 10 Drawing Sheets

U.S. PATENT DOCUMENTS

| | | | |
|---|---|---|---|
| 2006/0091571 A1 | 5/2006 | Akutsu et al. | 264/1.24 |
| 2006/0141617 A1* | 6/2006 | Desai et al. | 435/325 |
| 2008/0152281 A1* | 6/2008 | Lundquist et al. | 385/31 |
| 2010/0063404 A1* | 3/2010 | Kaplan et al. | 600/478 |

FOREIGN PATENT DOCUMENTS

| | | |
|---|---|---|
| JP | 2001 147301 A | 5/2001 |
| WO | 00/31752 A | 6/2000 |
| WO | 01/85637 A | 11/2001 |

* cited by examiner

BIOPOLYMER OPTICAL WAVEGUIDE AND METHOD OF MANUFACTURING THE SAME

CROSS-REFERENCE TO RELATED APPLICATIONS

This application is a 35 U.S.C. §371 National Stage of International Application No. PCT/US2007/083605 filed on Nov. 5, 2007, which designates the United States, and which claims the benefit of priority under 35 U.S.C. §119(e) of U.S. Provisional Application Ser. No. 60/856,297 filed on Nov. 3, 2006, the contents of which are incorporated herein by reference.

GOVERNMENT SUPPORT

The invention was made with government support under grant number EB002520 awarded by the National Institutes of Health, DMR0402849 awarded by the National Science Foundation, and FA95500410363 awarded by the Air Force Office of Scientific Research. The government has certain rights in this invention.

BACKGROUND OF THE INVENTION

1. Field of the Invention

The present invention is directed to biopolymer optical waveguides and methods for manufacturing such devices.

2. Description of Related Art

The field of optics is well established. Some subfields of optics include diffractive optics, micro-optics, photonics and guided wave optics. Various optical devices have been fabricated in these and other subfields of optics for research and commercial application. For example, common optical devices include diffraction gratings, photonic crystals, optofluidic devices, waveguides, and the like.

Optical waveguides are physical structures that guide electromagnetic waves in the optical spectrum. Common types of optical waveguides include optical fiber and rectangular waveguides. Optical waveguides are often used as components in integrated optical circuits or as the transmission medium in optical communication systems. Optical waveguides may be classified according to their geometry, such as planar, strip, or fiber waveguides. They may also be classified according to their mode structure, such as single-mode or multi-mode. Likewise, optical waveguides may be categorized according to their refractive index distribution, such as step or gradient index. Additionally, optical waveguides may also be classified according to their material composition, such as glass, semiconductor, or polymer.

These optical devices are fabricated using various methods depending on the application and optical characteristics desired. However, these optical devices, and the fabrication methods employed in their manufacture, generally involve significant use of non-biodegradable materials. For example, glass, fused silica, and plastic are commonly used in optical devices. Such materials are not biodegradable and remain in the environment for extended periods of time after the optical devices are removed from service and discarded. Of course, some of the materials can be recycled and reused. However, recycling also requires expenditures of natural resources, and adds to the environmental costs associated with such materials.

Therefore, there exists an unfulfilled need for optical waveguides that minimize the negative impact to the environment. In addition, there exists an unfulfilled need for optical waveguides that provide additional functional features that are not provided by conventional optical waveguides.

SUMMARY OF THE INVENTION

In view of the foregoing, objects of the present invention are to provide novel biopolymer optical waveguides and methods for manufacturing such optical waveguides that may be used in various applications.

One aspect of the present invention is to provide biopolymer waveguide devices.

Another aspect of the present invention is to provide a method for manufacturing such biopolymer waveguide devices.

One advantage of the present invention is in providing biopolymer waveguide devices that minimize the negative impact to the environment.

Another advantage of the present invention is in providing biopolymer waveguide devices that are biocompatible.

Yet another advantage of the present invention is in providing biopolymer waveguide devices that have additional functional features that are not provided by conventional optical waveguides.

In the above regard, inventors of the present invention recognized that biopolymers, and especially silk proteins, present novel structure and resulting functions. For example, from a materials science perspective, silks spun by spiders and silkworms represent the strongest and toughest natural fibers known and present various opportunities for functionalization, processing, and biocompatibility. Over five millennia of history accompany the journey of silk from a sought-after textile to a scientifically attractive fiber. As much as its features had captivated people in the past, silk commands considerable attention in this day and age because of its strength, elasticity, and biochemical properties. The novel material features of silks have recently been extended due to insights into self-assembly and the role of water in assembly. These insights, in turn, have led to new processing methods to generate hydrogels, ultrathin films, thick films, conformal coatings, three-dimensional porous matrices, solid blocks, nanoscale diameter fibers, and large diameter fibers.

Silk-based materials achieve their impressive mechanical properties with natural physical crosslinks of thermodynamically stable protein secondary structures also known as beta sheets (β-sheets). The high number of nanoscale aligned crystals (β-sheets), combined with highly hydrogen bonded, less crystalline domains leads to a unique structure and functional features. No exogenous crosslinking reactions or post-processing crosslinking is required to stabilize the materials. The presence of diverse amino acid side chain chemistries on silk protein chains facilitates coupling chemistry to functionalize silks, such as with cytokines, morphogens, and cell binding domains. There are no known synthetic or biologically-derived polymer systems that offer this range of material properties or biological interfaces, when considering mechanical profiles, aqueous processing, ease of functionalization, diverse modes of processing, self-forming crosslinks, biocompatibility, and biodegradability.

While no other biopolymer or synthetic polymer can match the range of features outlined above for silk, the inventors of the present invention have identified some other polymers that exhibit various properties similar or analogous to silk. In particular, other natural biopolymers including chitosan, collagen, gelatin, agarose, chitin, polyhydroxyalkanoates, pullan, starch (amylose amylopectin), cellulose, hyaluronic acid, and related biopolymers, or a combination thereof have been identified. In view of the above-noted features of biopolymers and of silk in particular, the present invention provides various novel biopolymer optical waveguides and methods for manufacturing such devices.

In accordance with one aspect of the present invention, one method of manufacturing a biopolymer optical waveguide includes providing a biopolymer, and casting the biopolymer in a second polymer to form a biopolymer optical waveguide. The second polymer forms a polymer overcoat cladding around the biopolymer. Because the biopolymer and the second polymer have different indices of refraction, the biopolymer may be used to guide light through the second polymer.

In one embodiment, the biopolymer may be silk, and silk fibers may be provided by unwinding the silk to extract individual biopolymer fibers. The unwound silk fibers may then be placed under tension in a tensioning or straightening device. The silk fibers may then be cast in the second polymer, such as polydimethylsiloxane (PDMS) or other suitable polymers. Because the silk fibers have a higher index of refraction (n=1.55) than the PDMS (n=1.46), the combination functions as a waveguide as the silk transmits light through the PDMS. Of course, other biopolymers such as chitosan, collagen, gelatin, agarose, chitin, polyhydroxyalkanoates, pullan, starch (amylose amylopectin), cellulose, hyaluronic acid, and related biopolymers, or a combination thereof may be used as long as the (second) polymer overcoat has a lower index of refraction than the selected biopolymer. In this fashion, the (second) polymer overcoat will serve as cladding material to the biopolymer core of the optical waveguide.

In another embodiment, raw silk fibers or extruded fibers may be pre-treated or otherwise treated to remove surface roughness using low-intensity laser ablation or other smoothing techniques. Similarly, the faces of the fibers may be ablated to provide a suitable optical surface for coupling light into the silk.

Waveguides of different geometries may be formed by the method of the present invention including concentric waveguides with circular cross-sectional area. Likewise, rectangular waveguides may be formed when the second polymer is deposited as a guiding layer of a slab waveguide and the biopolymer is cast between layers of the slab. Rectangular biopolymer optical waveguides manufactured in accordance with the present invention may be used in integrated optical circuits and as a host of optical devices. Rectangular biopolymer optical waveguides manufactured in accordance with the present invention may also be used as the basis of interferometers and wavelength division multiplexers.

In accordance with another embodiment of the present invention, biopolymer optical waveguides with rectangular geometry may be produced by a planar printing technique. In this embodiment, a method of manufacturing a biopolymer optical waveguide includes providing a substrate, printing a first biopolymer on the substrate, and depositing a second material on the first biopolymer to form the biopolymer optical waveguide, where the second material has a lower index of refraction than the first biopolymer. In one embodiment, the first biopolymer may be silk, while in other embodiments of the present invention, a protein may be printed on the substrate.

With silk and other biocompatible biopolymer optical waveguides, numerous biomedical applications are possible. For example, biocompatible organic optical fibers may be used in vivo for diagnostic light delivery and therapeutics. The biopolymer optical waveguides may be used as light-enabled nervous system replacement fibers for paralyzed or damaged neurons. The optical waveguides of the present invention may be inserted in the body as transmission media for optical radiation, and meshes of silk optical fibers can relay information from arrays of sensors or from different locations within the body.

Similarly, embedded silk fibers as material components can serve as nondestructive indicators of material damage, fatigue or failure, even in instances when the surface of the material appears fine. The method of the present invention allows silk fiber to be functionalized to enable preferential interaction between guided light and an organic optical fiber.

In addition, the biopolymer optical waveguide of the present invention may be used in additional applications. For example, the biopolymer optical waveguides may be used as sensors, as proteo-optofluidic devices, and as subclasses of these devices, including protein and virus detectors, flow cytometers, flow monitors, absorbers, specialized channels, cell sieves, and the like.

These and other advantages and features of the present invention will become more apparent from the following detailed description of the preferred embodiments of the present invention when viewed in conjunction with the accompanying drawings.

DETAILED DESCRIPTION OF THE INVENTION

As described in detail below, the biopolymer optical waveguide devices in accordance with the present invention have been fabricated using a biopolymer such as silk. In this regard, the silk utilized was silkworm silk. However, there are many different silks, including spider silk, transgenic silks, and genetically engineered silks, variants and combinations thereof and others, that may alternatively be used in accordance with the present invention to obtain a biopolymer optical waveguide device.

In addition, other biodegradable polymers may be used instead of silk. For example, additional biopolymers, such as chitosan, exhibit desirable mechanical properties, can be processed in water, and form generally clear films for optical applications. Other biopolymers, such as chitosan, collagen, gelatin, agarose, chitin, polyhydroxyalkanoates, pullan, starch (amylose amylopectin), cellulose, hyaluronic acid, and related biopolymers, or a combination thereof, may alternatively be utilized in specific applications and combinations, and synthetic biodegradable polymers such as polylactic acid, polyglycolic acid, polyhydroxyalkanoates and related copolymers may also be selectively used. Some of these polymers are not as easily processed in water. Nonetheless, such polymers may be used by themselves, in combination with other polymers, or in combinations with silks, and may be used in particular biopolymer optical devices.

Figure 1:
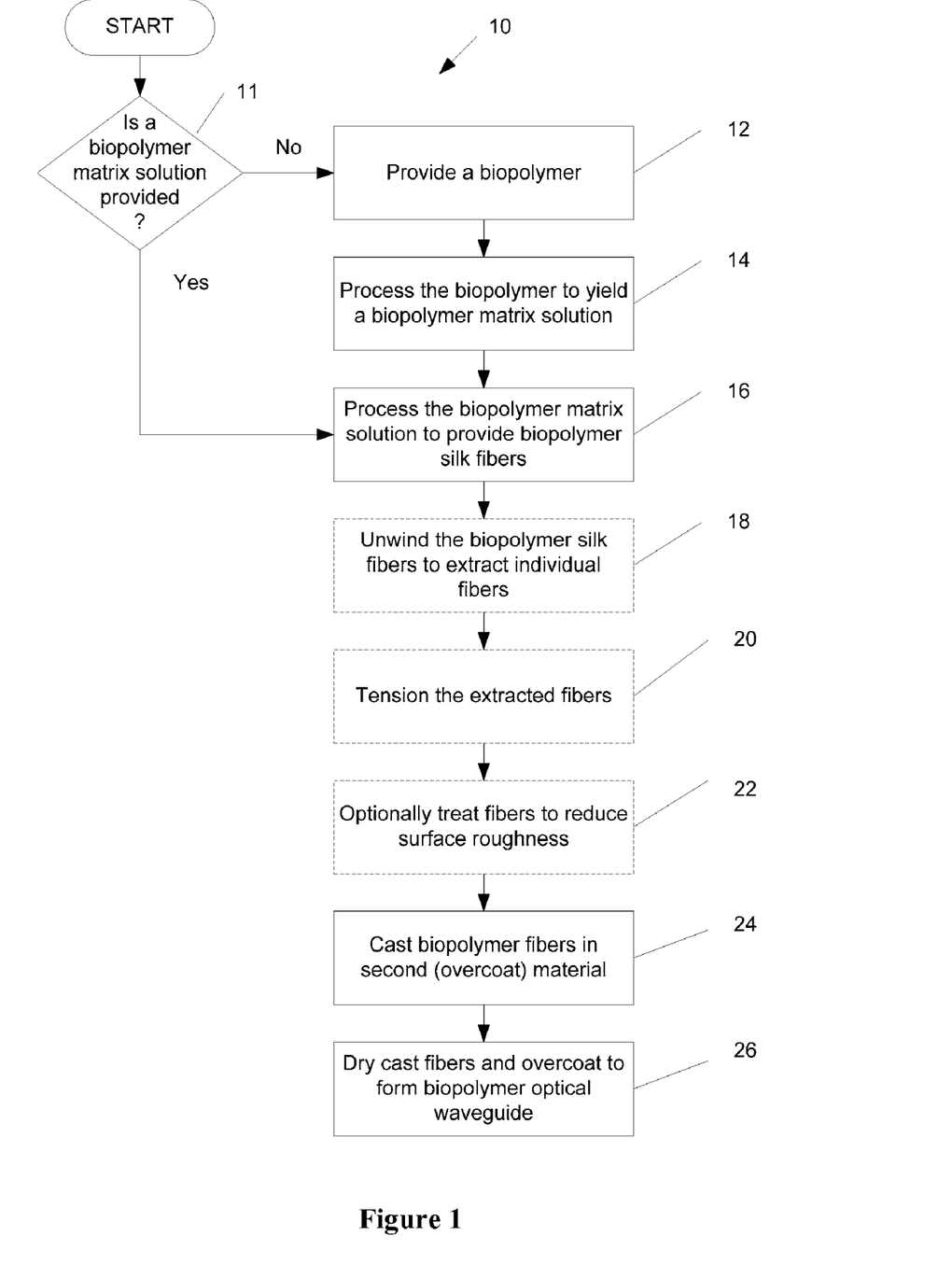
FIG. 1 is a schematic flow diagram illustrating a method in accordance with one embodiment of the present invention.

FIG. 1 is a schematic illustration of a flow diagram 10 showing a method of manufacturing a biopolymer optical waveguide in accordance with one embodiment of the present invention. If a biopolymer matrix solution is provided in step 11, the process proceeds to step 16 below. Otherwise, a biopolymer is provided in step 12. In the example where the biopolymer is silk, the biopolymer may be provided by extracting sericin from the cocoons of *Bombyx mori*. In step 14, the biopolymer is processed to yield a biopolymer matrix solution.

In step 16, the biopolymer matrix solution is processed to provide biopolymer silk fibers, raw silk fibers or extruded fibers. In the example of silk, an aqueous silk fibroin solution is processed in step 16, for example, 8.0 wt %, which is then used to manufacture the biopolymer optical waveguide. Of course, in other embodiments, the solution concentrations may also be varied from very dilute (approximately 1 wt %) to very high (up to 30 wt %) using either dilution or concentration, for example, via osmotic stress or drying techniques. In this regard, other embodiments may utilize different percent weight solutions to optimize flexibility or strength of the resultant biopolymer optical waveguide, depending on the application. Production of aqueous silk fibroin solution is described in detail in WIPO Publication Number WO 2005/012606 entitled "Concentrated Aqueous Silk Fibroin Solution and Uses Thereof".

If biopolymer silk fibers are provided, the silk fibers may be unwound progressively to extract individual silk fibers in optional step 18. In optional step 20, the unwound biopolymer (silk) fibers are placed under tension using a tensioning or straightening device, such as framing elements, turnbuckles, clamp sets, and the like.

The fibers can also be formed synthetically as disclosed in WO04000915A2, entitled "Silk Biomaterials and Methods of Use Thereof;" WO9315244A1 entitled "Fiber-Spinnable Solutions Of Silkworm Fibroin;" and/or U.S. Pat. No. 5,252,285 entitled "Process For Making Silk Fibroin Fibers," all being herein incorporated by reference.

In optional step 22, the silk biopolymer raw silk fibers or extruded fibers may be treated to remove surface roughness. This optional smoothing treatment may be performed using low-intensity laser ablation techniques, or using other smoothing techniques to reduce or remove surface roughness. Additionally, the faces of the silk biopolymer raw or extruded fibers may be ablated to provide an improved optical surface for coupling light into the silk core.

In step 24, the fibers are cast in a second polymer, such as polydimethylsiloxane (PDMS), or the like, which acts as a polymer overcoat to form a biopolymer optical waveguide. Of course other materials may also be used with which to form the over coat of the biopolymer fiber core. In step 26, the cast fibers and polymer overcoat are dried, and the method of manufacturing the biopolymer optical waveguide is complete.

Figure 2:
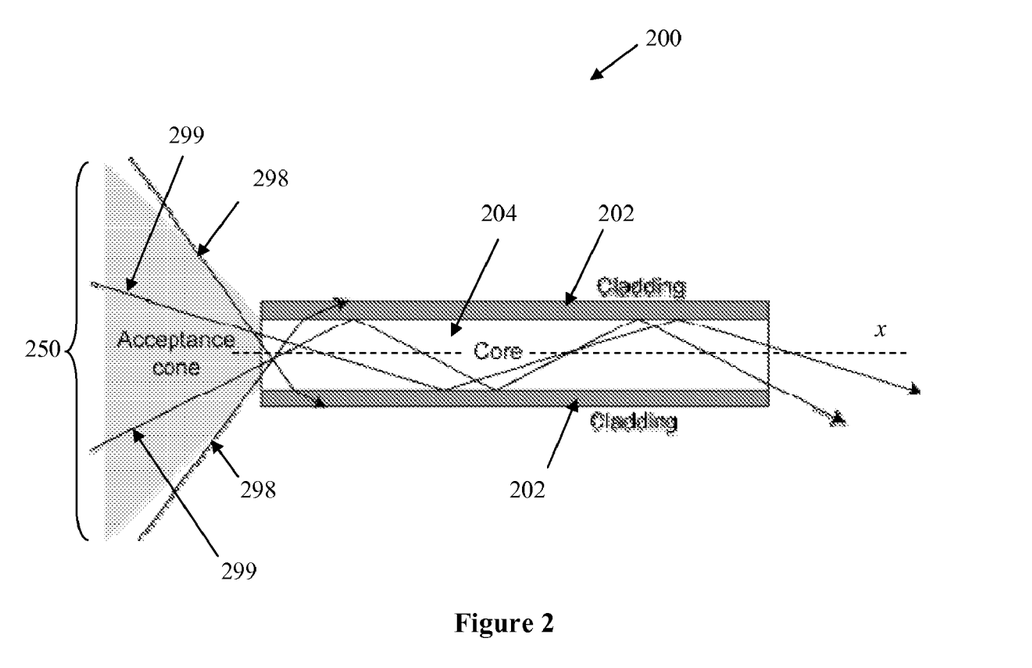
FIG. 2 is a schematic diagram of a biopolymer optical waveguide manufactured in accordance with one embodiment of the present invention.

As illustrated schematically in FIG. 2, the second material 202 forms a polymer overcoat cladding around the biopolymer. Because the biopolymer silk fibers have a higher index of refraction (n=1.55) than the PDMS overcoat cladding (n=1.46), the combination functions as a waveguide 200 as the silk biopolymer fibers act as a core 204 to transmit light waves (shown as arrows 298, 299) through the second material 202. Of course, other biopolymers such as chitosan, collagen, gelatin, agarose, chitin, polyhydroxyalkanoates, pullan, starch (amylose amylopectin), cellulose, hyaluronic acid, and related biopolymers, or a combination thereof may be used as the core 204 as long as the second material (overcoat) 202 has a lower index of refraction than the selected biopolymer. In this fashion, the second material 202, such as the PDMS polymer overcoat, will serve as cladding material 202 to the biopolymer core 204 of the optical waveguide 200.

FIG. 2 illustrates how light waves 298, 299 are guided through the biopolymer optical waveguide 200 of the present invention. Incident rays 299 of light that fall within the acceptance cone 250 of the biopolymer fiber core 204 are transmitted through the waveguide 200, whereas those incident light rays 298 that fall outside of the acceptance cone 250 of the biopolymer fiber core 204 are lost in the second material cladding 202.

As shown in FIG. 2, the biopolymer optical waveguide 200 of the present invention may be manufactured in a longitudinal geometry with a circular cross-section, where the biopolymer core 204 and the second material overcoat cladding 202, such as PDMS, form a concentric biopolymer waveguide 200 along a longitudinal axis, x.

Figure 3A:
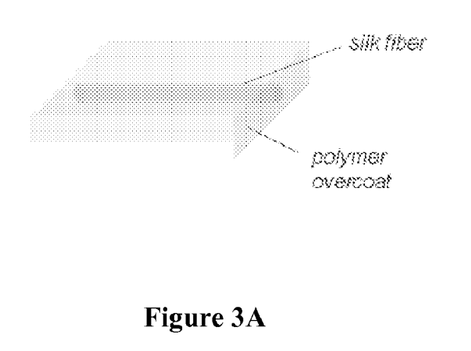
FIG. 3A is a schematic illustration of a biopolymer optical waveguide in accordance with the present invention.
Figure 3B:
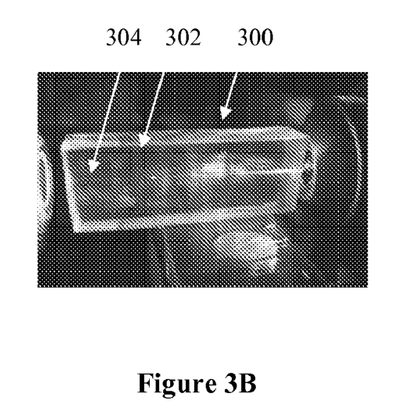
FIG. 3B is a photograph of a biopolymer optical waveguide in accordance with the present invention.

FIG. 3A shows a schematic illustration, and FIG. 3B shows a photograph of a biopolymer optical waveguide 300 made of silk in accordance with one embodiment of the present invention. As described above, the silk fiber 304 is embedded in a polymer overcoat material 302. The index of refraction of the silk fiber 304 enables the realization of the waveguide 300 by virtue of the index contrast between the silk fiber 304 and the surrounding polymer overcoat material 302, which in the example shown in FIG. 3B, is PDMS.

Figure 4:
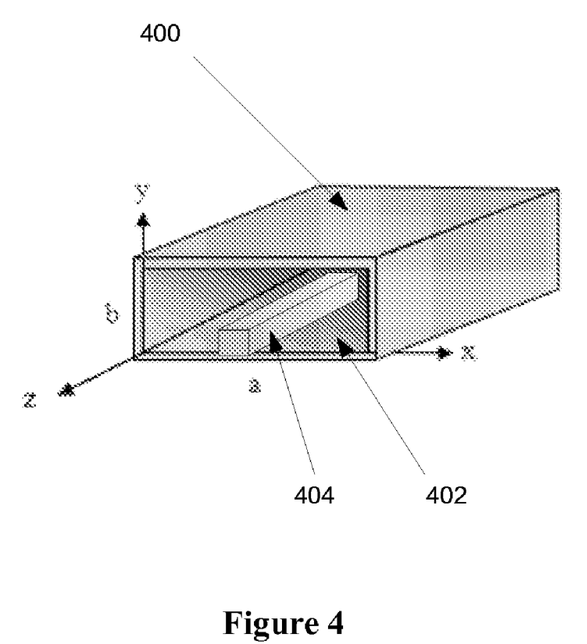
FIG. 4 is a schematic diagram of a biopolymer optical waveguide manufactured in accordance with another embodiment of the present invention.

Of course, the biopolymer optical waveguide of the present invention may be manufactured with additional geometries as well. For example, the biopolymer optical waveguide may include a first biopolymer 404 and a polymer overcoat 402 that form a rectangular slab waveguide 400 along a planar axis (Z-axis) as shown in FIG. 4.

Waveguides of different geometries may be formed by the method of the present invention including concentric waveguides with circular cross-sectional area as illustrated in FIG. 2. Likewise, rectangular waveguides as shown in FIG. 4 may be formed when the second polymer 402 is deposited as a guiding layer of a slab waveguide 400 and the biopolymer 404 is cast between layers of the slab. Rectangular biopolymer optical waveguides manufactured in accordance with the present invention may be used in integrated optical circuits and as a host of optical devices. Rectangular biopolymer optical waveguides manufactured in accordance with the present invention may also be used as the basis of interferometers and wavelength division multiplexers.

The physical parameters of a rectangular waveguide help determine the electrical operating characteristics. The dimension of the broad wall a in FIG. 4 influences the frequency range of operation, while the dimension of the narrow wall b serves to establish the breakdown voltage of the wave guide and likewise the peak power handling capability.

In addition to uses as in vivo diagnostic light delivery components and therapeutic delivery components, the optical fibers of the present invention may be inserted in the body as transmissive media for optical radiation, and meshes of silk optical fibers may relay information from sensors or from different locations within the body.

Similarly, embedded silk fibers may serve as nondestructive indicators of material damage, fatigue, and failure, even when the outward appearance of the material surface shows no damage.

Figure 5:
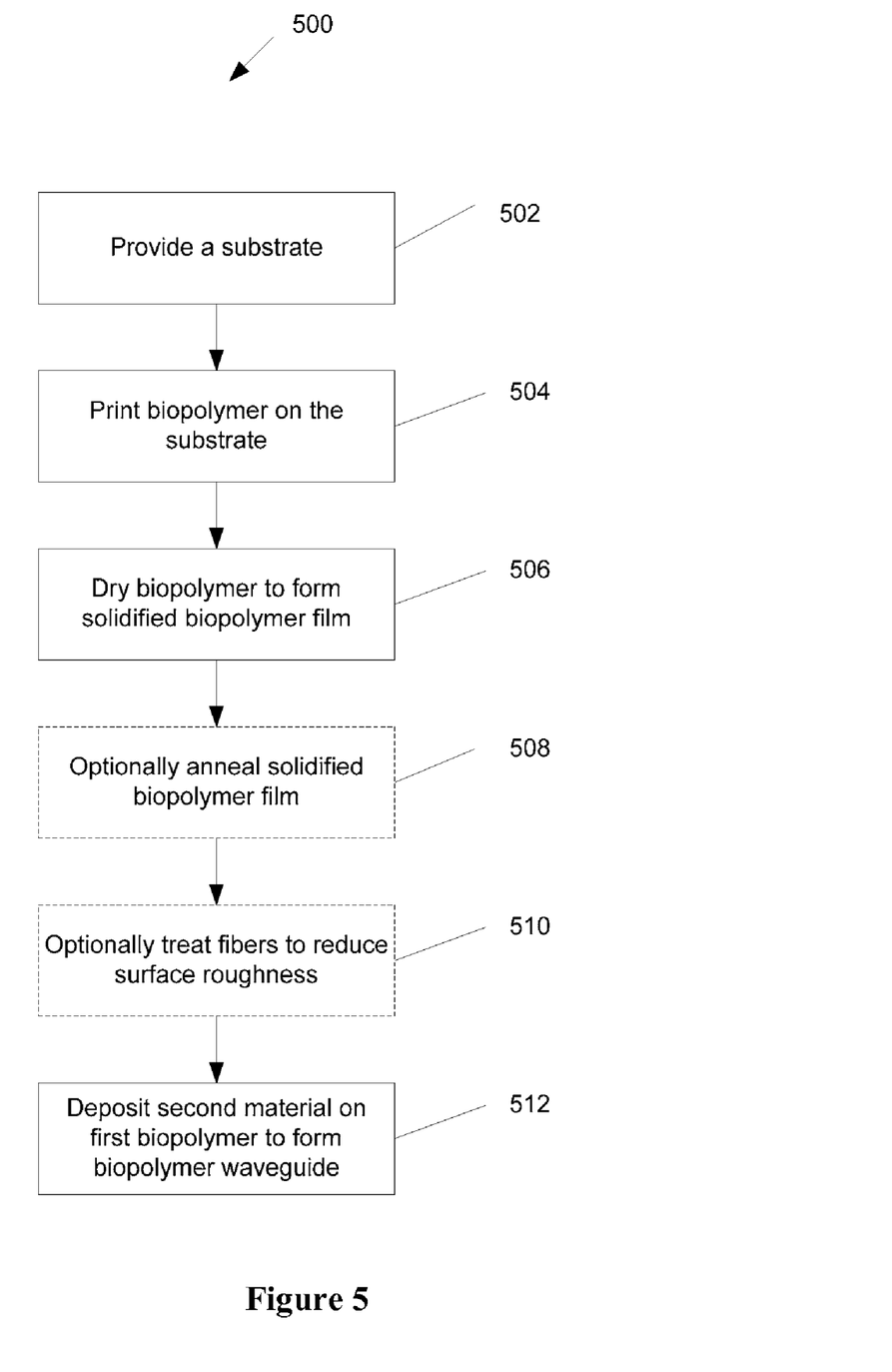
FIG. 5 is a schematic flow diagram illustrating a method in accordance with one embodiment of the present invention.

In accordance with another embodiment of the present invention, biopolymer optical waveguides with rectangular geometry may be produced by a planar printing technique. This embodiment is illustrated in FIG. 5, where a method of manufacturing a biopolymer optical waveguide 500 includes providing a substrate in step 502.

The substrate may be a template for an optical device, such as a lens, a microlens array, an optical grating, a pattern generator, a beam reshaper, and other optical devices. The substrate provided in step 502 serves as a mold in manufacturing the biopolymer optical device, which in the above example is a waveguide. A surface of the substrate has the desired characteristic features to be formed on the biopolymer optical device. In this regard, the substrate may be an appropriate nanopattern on a surface of the optical device and may be an optical device such as a nanopatterned optical grating, depending on the optical features desired for the biopolymer optical device being manufactured.

In step 504, a first biopolymer is printed on the substrate. The first biopolymer may be printed on the substrate using ink jet style printing. An aqueous biopolymer matrix solution may be used as the first biopolymer print medium cast upon the substrate by the printing process. The aqueous biopolymer matrix solution may then be dried in step 506 to transition the aqueous biopolymer matrix solution to the solid phase. In this regard, the aqueous biopolymer matrix solution may be dried for a period of time such as 24 hours, and may optionally be subjected to low heat to expedite drying of the aqueous biopolymer matrix solution. Upon drying, a solidified biopolymer film is formed on the surface of the substrate. The thickness of the biopolymer film depends on the volume of the biopolymer matrix solution applied to the substrate.

Once the solvent of the biopolymer matrix solution has evaporated, the solidified biopolymer film may optionally be annealed in step 508. This annealing step may be performed within a water vapor environment, such as in a chamber filled with water vapor, for different periods of time depending on the material properties desired. Typical annealing time periods may range from between two hours to two days, for example, and may also be performed in a vacuum environment, or in a combination of environments. After an appropriate drying time, the biopolymer film is a suitable printed silk biopolymer layer.

In optional step 510, the printed silk biopolymer layer may be treated to remove surface roughness. This optional smoothing treatment may be performed using low-intensity laser ablation techniques, or using other smoothing techniques to reduce or remove surface roughness. Additionally, the faces of the silk biopolymer layer may be ablated to provide an improved optical surface for coupling light into the silk core.

In step 512, a second material is deposited on the first biopolymer to form the biopolymer optical waveguide. The second material has a lower index of refraction than the first biopolymer. In one embodiment, the first biopolymer may be silk, while in other embodiments of the present invention, a protein may be printed on the substrate. Similarly, in one embodiment, the second lower index of refraction material is polydimethylsiloxane (PDMS), while in other embodiments, other materials may be utilized.

As illustrated above and schematically in FIG. 5, the second material forms a polymer overcoat cladding around the biopolymer. Because the biopolymer silk fibers have a higher index of refraction (n=1.55) than the PDMS overcoat cladding (n=1.46), the combination functions as a waveguide as the silk biopolymer fibers act as a core to transmit light through the second material. Of course, other biopolymers such as chitosan, collagen, gelatin, agarose, chitin, polyhydroxyalkanoates, pullan, starch (amylose amylopectin), cellulose, hyaluronic acid, and related biopolymers, or a combination thereof, may be used as long as the second material (overcoat) has a lower index of refraction than the selected biopolymer. In this fashion, the second material, such as the PDMS polymer overcoat, will serve as cladding material to the biopolymer core of the optical waveguide.

The first biopolymer material may be deposited on the substrate in any efficient manner. For example, the first biopolymer material may be printed onto the substrate using inkjet technology, such as with an inkjet-style printer. The first biopolymer may be printed on the substrate by forming a layer of various thicknesses of the first biopolymer. The printing of the first biopolymer may be repeated using overlay printing techniques to increase the thickness of the biopolymer waveguide, depending upon the desired application. The (second) lower index of refraction material is then deposited on top of the printed silk core. As mentioned above, a protein or other biopolymer with a higher index of refraction may also be used as the core material of the waveguide.

Figure 6:
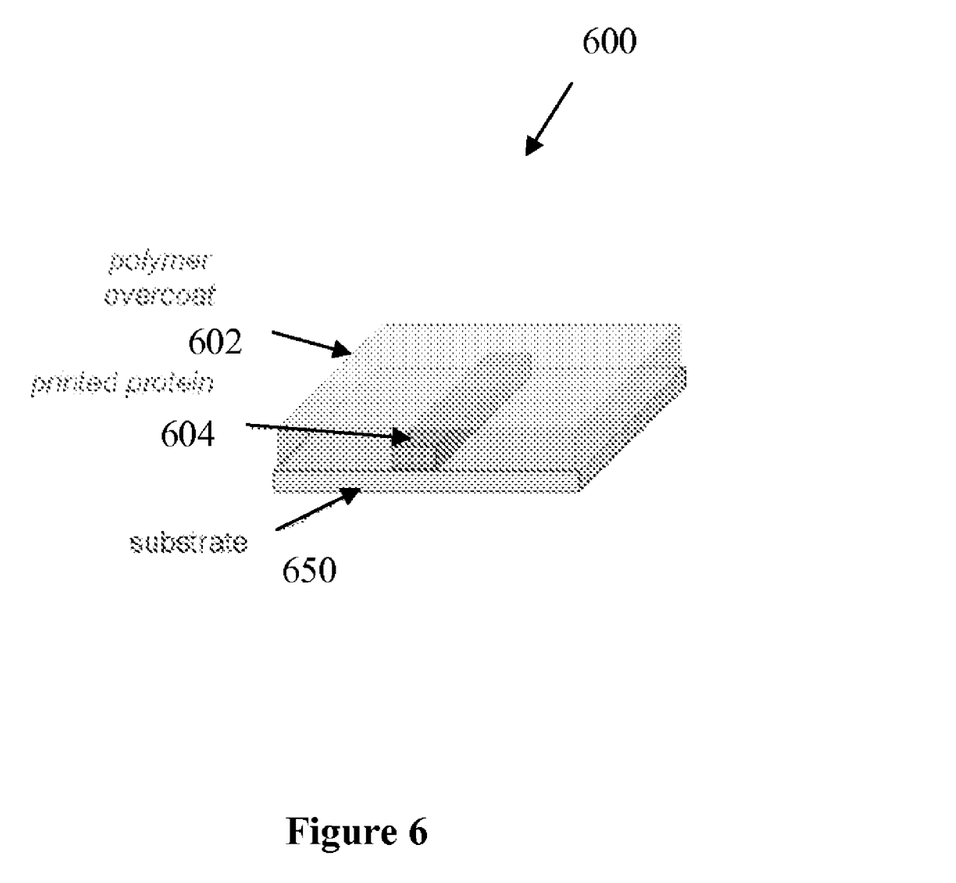
FIG. 6 is a schematic illustration of a biopolymer optical waveguide manufactured in accordance with one embodiment of the present invention that uses printed proteins to form channels of the waveguide.

The above printing embodiment is shown schematically in FIG. 6. As shown, a substrate 650 is provided, and the protein waveguide core 604 is printed on the substrate 650 using inkjet technology. A lower index of refraction 602 material is then deposited on top of the printed protein waveguide core 604. Inkjet application may be used to print the materials based on experimental dimensions of the desired printed protein waveguide. As indicated above, overlay printing of the individual lines of the printed protein waveguide core 604 may be necessary to build up the thickness of the biopolymer waveguide.

Figure 7:
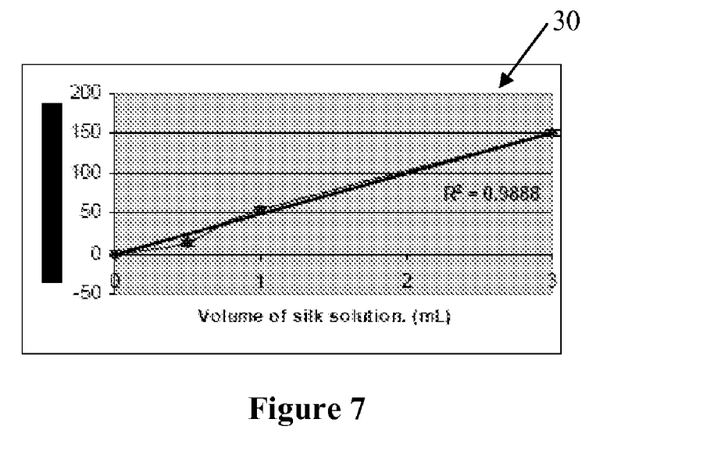
FIG. 7 is a graph that illustrates the relationship between the volume of 8% silk concentration vs. film thickness.

Experiments were conducted to validate the above-described method by manufacturing various biopolymer optical waveguides. The relationship between the volume of 8 wt % silk concentration aqueous silk fibroin solution, and the resulting silk film thickness, is shown in the graph 30 of FIG. 7, where the aqueous silk fibroin solution was cast over a substrate surface of approximately 10 square centimeters. The X-axis shows the volume of silk fibroin solution in mL, and the Y-axis shows the thickness of the resultant film in μm.

Of course, the film properties such as thickness and biopolymer content, as well as optical features, may be altered based on the concentration of fibroin used in the process, the volume of the aqueous silk fibroin solution deposited, and the post-deposition process for drying the cast solution to lock in the structure. Accurate control of these parameters is desirable to ensure the optical quality of the resultant biopolymer optical waveguide and to maintain various characteristics of the biopolymer optical waveguide, such as transparency, structural rigidity, and flexibility. Further-more, additives to the biopolymer matrix solution may be used to alter features of the biopolymer optical waveguide such as morphology, stability, and the like, as known with polyethylene glycols, collagens, and the like.

Figure 8A:
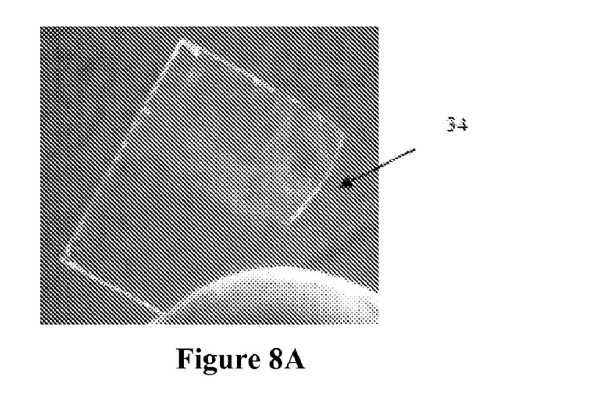
FIG. 8A is a photograph of a biopolymer film made of silk.
Figure 8B:
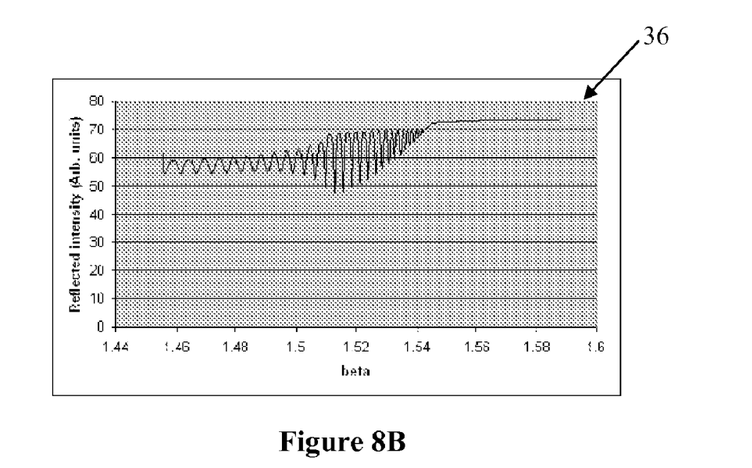
FIG. 8B is a graph showing the prism coupled angular dependence of reflectivity of the biopolymer film of FIG. 8A.

An unpatterned biopolymer film having a thickness of 10 μm was manufactured in the above-described manner using an aqueous silk fibroin solution, and was characterized in a scanning prism coupled reflectometer from Metricon Corporation. FIG. 8A illustrates the unpatterned biopolymer film 34 manufactured and characterized. The index of refraction of the biopolymer film 34 was measured to be n=1.55 at 633 nm, which is slightly higher than the index of refraction of conventional borosilicate glass. The measured index of refraction confirms that the value is high enough to afford reasonable contrast for optical use such as in air-silk biophotonic crystals (BPC) ($\Delta n_{fibroin} - \Delta n_{air} = 0.55$). The characterization of the unpatterned silk film 34 is shown in graph 36 of FIG. 8B, which clearly demonstrates the prism coupled angular dependence of the reflectivity. The oscillations in graph 36 are due to coupling into guided waves, demonstrating the use of silk as a waveguide material.

Figure 8C:
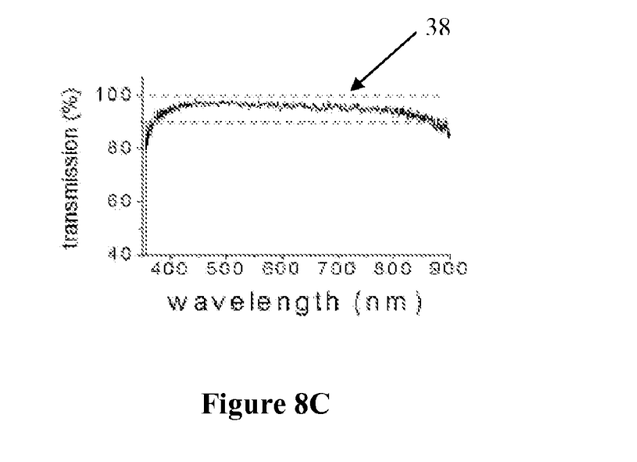
FIG. 8C is a graph showing he measured transmission of light through the biopolymer film of FIG. 8A.

In addition, the unpatterned silk film 34 was also analyzed to determine transparency. FIG. 8C is a graph 38 that illustrates the measured transmission of light through the silk film 34 in various wavelengths. Transmission measurements indicate that the unpatterned silk film 34 was highly transparent across the visible spectrum. For comparison, similar thickness films were also cast in collagen, and polydimethylsiloxane (PDMS). The free-standing structural stability was found to be inferior, and the resultant biopolymer optical device was not self-supporting when implemented as a thin film. However, such biopolymers may be used in other applications if structural stability is deemed to be not as important.

Importantly, shaped films having various thicknesses were patterned on the nanoscale using the methods of FIG. 1 and FIG. 5 described above to provide nanopatterned biopolymer optical devices.

The term "nanopatterned" as used with regard to the present invention refers to very small patterning that is provided on a surface of the biopolymer optical device. The patterning has structural features whose size can be appropriately measured on a nanometer scale (that is, $10^{-9}$ meters), for example, sizes ranging from 100 nm to few microns. Additionally, the biopolymer optical devices of the present invention may incorporate various different optical devices such as lenses, diffraction gratings, photonic crystals, waveguides, and the like.

A variety of nanopatterned biopolymer optical devices were successfully manufactured using the above-described method of the present invention using silk fibroin solution. These devices included waveguides, lenses, microlens arrays, optical gratings, pattern generators, and beam reshapers. In particular, the aqueous solution of silk fibroin was cast onto specific substrates with patterns thereon. The substrate surfaces were coated with Teflon™ to ensure even detachment after the biopolymer matrix solution transitions from the liquid to the solid phase. The ability of the biopolymer casting method of the present invention for forming highly defined nanopatterned structures in biopolymer optical devices was verified by casting the optical waveguides of the present invention. Regular patterned features with dimensions down to 210 nm, and localized surface roughness of less than 20 nm, have been attained. As mentioned above, smoothing techniques may also be used to further reduce or remove surface roughness of the biopolymer optical waveguide.

The measured roughness of cast silk film on an optically flat surface shows measured root mean squared roughness values between 2.5 and 5 nanometers, which implies a surface roughness easily less than $\lambda/50$ at a wavelength of 633 nm. Atomic force microscope images of patterned silk diffractive optics show the levels of microfabrication obtainable by casting and lifting silk films off of appropriate molds. The images show definition in the hundreds of nanometer range and the sharpness of the corners indicates the possibility of faithful patterning down to the tens of nanometers.

Optical losses through a silk slab waveguide obtained by guiding 633 nm light through pure silk films of variable thickness were measured. The optical loss measurements varied from 0.25 to 0.75 dB/cm depending on the scattering of the film. With control of the purity of the silk solution and of the homogeneity of the layers throughout the surface losses can be further diminished to values well below those measured.

Such regular patterning of biocompatible materials allows manufacturing of optical devices that can be used to provide photonic bandgaps and manipulate light via an organic, yet mechanically robust optical device. These devices combine the flexibility of embedded optics with the unique versatility of the protein substrate as explained throughout the application. Many advantages are provided by the present invention including combining the organic nature of biopolymers such as silk with the power of diffractive and transmissive optics embedded in an organic matrix to create biologically active optical elements. Silk provides a controllably degradable, biocompatible, and structurally strong medium with which to fabricate the optical devices in accordance with the present invention.

Transmissive nanopatterned diffractive biopolymer optical devices were made using the method of the present invention described above. These optical devices include biopolymer optical waveguides, silk diffusers, line pattern generators, and cross pattern generators. Such optical devices use appropriately configured wavelength scale surface structuring to create predefined one or two-dimensional light patterns that exploit light interference. Such optical devices made of conventional materials have been applied to imaging, spectroscopy, beam sampling and transformation, and metrology to name a few uses. Extending this approach to control the delivery of light within a biological matrix such as silk biopolymer can provide optimal coupling of photons into a substrate or allow for designed optical discrimination, interface, or readout.

A significant advantage of biopolymer optical waveguides in accordance with the present invention is the ability of the optical waveguides to be biologically activated since they are entirely organic and biocompatible. Water-based processing can be used, for example, for silk optical waveguides. This increases cellular survivability of the waveguides and the likelihood of biocompatibility.

To confirm biocompatibility of nanopatterned biopolymer optical devices, red blood cells (RBCs) were incorporated into a silk diffraction grating in accordance with the present invention that was manufactured as described above with regard to FIG. 1 and FIG. 5. The RBC-silk fibroin solution was prepared by combining 1 ml of an 80% hematocrit human RBC solution and 5 ml of the 8% silk solution. The mixture was cast on a 600 lines/mm optical grating and allowed to dry overnight. The film was removed from the optical grating and annealed for two hours. The grating structure was observed in the resultant RBC-doped silk diffraction grating.

Figure 9:
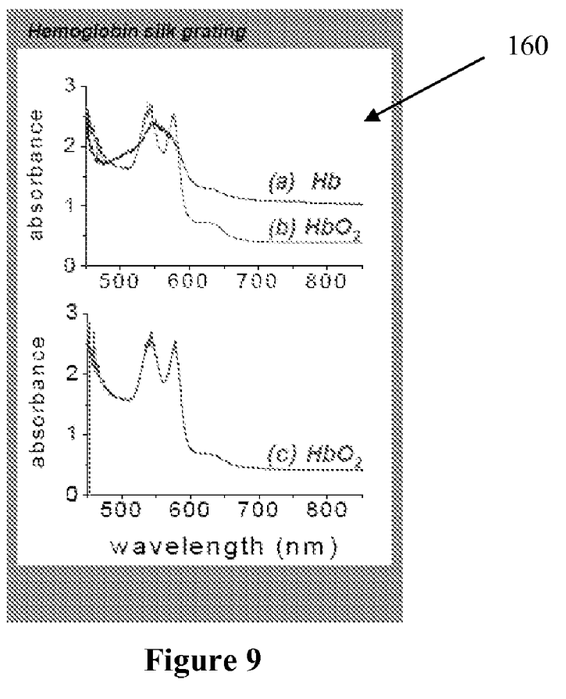
FIG. 9 illustrates results graphs showing retention of the hemoglobin function within an RBC-doped silk optical device.

The RBC-doped silk diffraction grating was then tested to observe the diffraction orders. An optical transmission experiment was performed to determine whether hemoglobin (the oxygen-carrying protein contained in RBCs) maintained its activity within the matrix of the silk diffraction grating. The results graphs 160 are shown in FIG. 9 and indicate the retention of hemoglobin function within the RBC-doped silk diffraction grating. The X-axis corresponds to the wavelength (in nm), and the Y-axis indicates the absorbance by the RBC-doped silk diffraction grating.

In particular, the RBC-doped silk diffraction grating was inserted in a quartz cuvette filled with distilled water, and an absorbance curve was observed. This result is shown by line (b) $HbO_2$ in results graphs 160. As can be seen, the absorbance curve shown by line (b) $HbO_2$ exhibited two peaks typical of oxy-hemoglobin absorption. Subsequently, nitrogen gas was bubbled into the cuvette to deoxygenate the hemoglobin. After 15 minutes, the characteristic absorption peaks of oxy-hemoglobin disappeared from the absorbance curve. This result is shown by line (a) Hb in the results graphs 160. These results were further confirmed when the nitrogen flow to the cuvette is subsequently halted, which resulted in the reappearance of the oxy-hemoglobin peaks. This result is shown by line (c) $HbO_2$ in results graphs 160.

Figure 10:
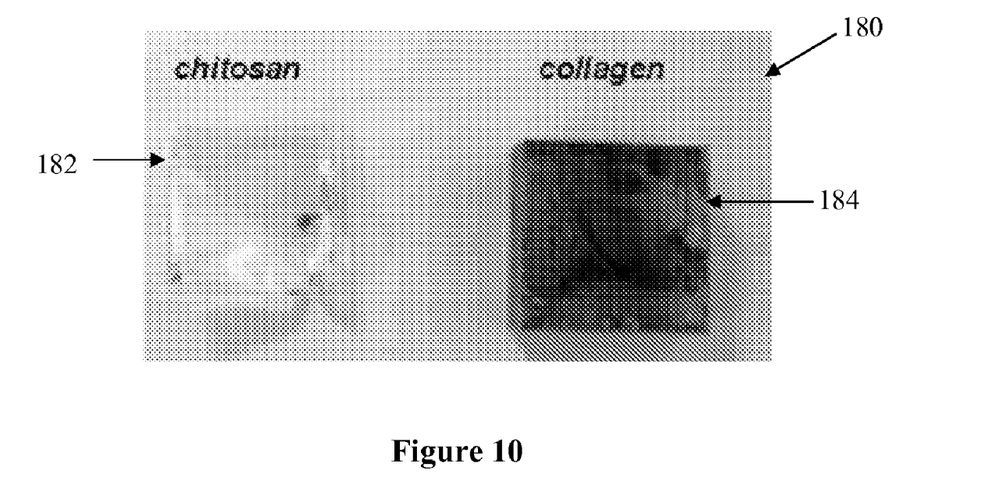
FIG. 10 is a photograph showing diffractive biopolymer devices that have been cast in silk, chitosan, and collagen.

As previously noted, alternative biopolymers may also be used for fabrication of nanopatterned biopolymer optical devices in accordance with the present invention. FIG. 10 shows a photograph 180 that illustrates other diffractive biopolymer optical devices that have been cast using different materials. In particular, a chitosan optical device 182 and a collagen optical device 184 have also been manufactured in accordance with the present invention. With respect to chitosan, optical diffraction characteristics similar to silk have been observed.

It should be evident from the above discussion and the example nanopatterned biopolymer optical devices shown and discussed that the present invention provides biodegradable nanopatterned biopolymer optical devices. High quality nanopatterned biopolymer optical devices were manufactured that are naturally biocompatible, can be processed in water, and can undergo degradation with controlled lifetimes. As explained above, the nanopatterned biopolymer optical devices of the present invention may also be biologically activated by incorporating small organic materials. For example, the small organic materials may be complex proteins such as hemoglobin in the red blood cells and enzymes such as peroxidase. The present invention broadens the versatility of optical devices by allowing the direct incorporation of labile biological receptors in the form of peptides, enzymes, cells, antibodies, or related systems, and allows such optical devices to function as biological sensing devices. Thus, the organic material can be a nucleic acid, a dye, a cell, an antibody, as described further in Appendix I, enzymes, for example, peroxidase, lipase, amylose, organophosphate dehydrogenase, ligases, restriction endonucleases, ribonucleases, DNA polymerases, glucose oxidase, laccase, cells, viruses, bacterias, proteins, peptides for molecular recognition, small molecules, drugs, dyes, amino acids, vitamins, antixoxidants, plant cells, mammalian cells, and the like, DNA, RNA, RNAi, lipids, nucleotides, aptamers, carbohydrates, optically-active chromophores including beta carotene or porphyrins, light emitting organic compounds such as luciferin, carotenes and light emitting inorganic compounds, chemical dyes, antibiotics, yeast, antifungals, antivirals, and complexes such as hemoglobin, electron transport chain coenzymes and redox components, light harvesting compounds such as chlorophyll, phycobiliproteins, bacteriorhodopsin, protorhodopsin, and porphyrins and related electronically active compounds, or a combination thereof.

The nanopatterned biopolymer optical devices of the present invention can be readily used in environmental and life sciences where biocompatibility and biodegradability are paramount. For example, the nanopatterned biopolymer optical devices as described above can be unobtrusively used to monitor a natural environment such as in the human body and may be implanted in vivo without a need to retrieve the device at a later time. The degradation lifetime of the nanopatterned biopolymer optical devices of the present invention can be controlled during the manufacturing process, for example, by controlling the ratio and amount of the solution matrix cast. Moreover, the nanopatterned biopolymer optical devices of the present invention can be dispersed in the environment, again without the need to retrieve them at a later time, thereby providing novel and useful devices for sensing and detection.

The foregoing description of the aspects and embodiments of the present invention provides illustration and description, but is not intended to be exhaustive or to limit the invention to the precise form disclosed. Those of skill in the art will recognize certain modifications, permutations, additions, and combinations of those embodiments are possible in light of the above teachings or may be acquired from practice of the invention. Therefore the present invention also covers various modifications and equivalent arrangements that fall within the purview of the appended claims.

Antibody Stability in Silk Films

Materials—Anti-IL-8 monoclonal antibody (IgG1) was purchased from eBioscience, Inc. human polyclonal antibody IgG and human IgG ELISA Quantitation Kit were purchased from Bethyl Laboratories Inc. All other chemicals used in the study were purchased from Sigma-Aldrich (St. Louis, Mo.).

Figure 11A:
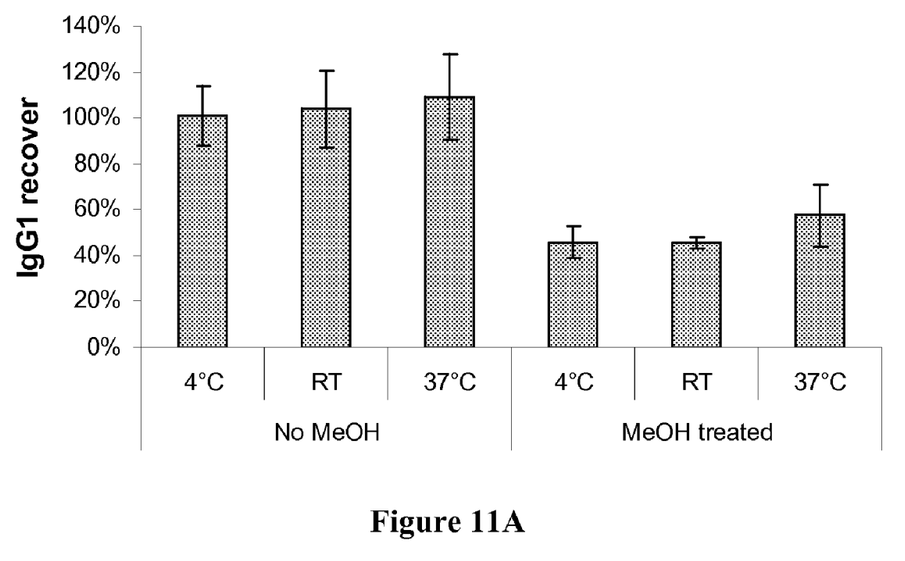
FIG. 11A: antibody IgG1 activity related to initial activity in the silk films prepared in the two different formats and stores at the three different temperatures.
Figure 11B:
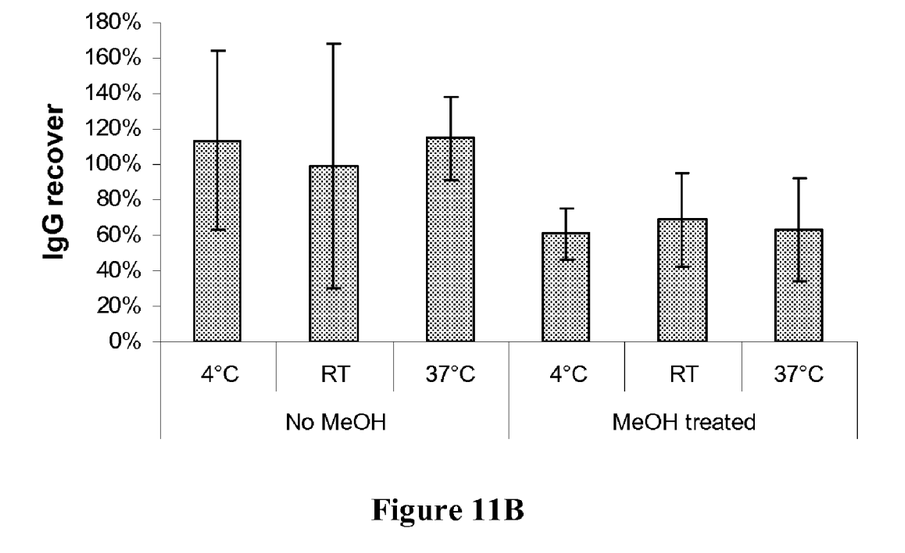
FIG. 11B: antibody IgG activity related to initial activity in the silk films prepared in the two different formats and stored at the three different temperatures.

Antibody entrapment in silk films—human polyclonal antibody IgG—Ten ml 1 mg/ml IgG mixed with 167 ml 6% silk solution make the IgG concentration in silk film mg/g silk. 100 µl of mixed IgG solution was added to each well of 96 well plate which was placed in a fume hood with cover opened overnight. The dried film was either treated or not treated with methanol. For methanol treatment, the wells were immersed in 90% methanol solution for 5 min and dried in the fume hood. All dry 96 well plates were then stored at 4° C., room temperature, and 37° C. (FIG. 11B).

Anti-IL-8 monoclonal antibody (IgG1)—0.5 ml 1 mg/ml IgG1 mixed with 83 ml 6% silk solution make the IgG1 concentration in silk film 0.1 mg/g silk. 50 µl of mixed IgG1 solution was added to a well of 96 well plate which was placed in a fume hood with cover opened overnight. The dried film was either treated or not treated with methanol. For methanol treatment, the wells were immersed in 90% methanol solution for 5 min and dried in the fume hood. All dry 96 well plates were then stored at 4° C., room temperature, and 37° C. (FIG. 11A).

Antibody measurement—Five wells prepared at the same condition were measured for statistic. Pure silk (without antibody) was used as a control.

For non methanol-treated samples, 100 µl of PBS buffer, pH 7.4, was added to the well which was further incubated at room temperature for 30 min to allow the film to completely dissolve. Aliquot of solution was then subjected to antibody measurement. For methanol-treated samples, 100 µl HFIP was added into each well which was further incubated at room temperature for 2 hours to allow the film completely dissolve. The silk HFIP solution was dried in a fume hood overnight. The follow step was the same as non methanol-treated samples, added PBS buffer and pipette the solution for antibody measurement.

ELISA—Polystyrene (96-well) microtitre plate was coated with 100 µL of antigen anti-Human IgG-affinity at a concentration of 10 µg/mL prepared in antigen coating buffer (bicarbonate buffer, 50 mM, pH 9.6) and then incubated overnight storage at room temperature. The wells were then washed three times with TBS-T buffer. The unoccupied sites were blocked with 1% BSA in TBS (200 µL each well) followed by incubation for 30 minutes at room temperature. The wells were then washed three times with TBS-T. The test and control wells were then diluted with 100 µL of serially diluted serum. Each dilution was in TBS buffer. Serially diluted blanks corresponding to each dilution were also present. The plate was then incubated for 1 h at room temperature. The plate was washed again with TBS-T buffer (five times). Bound antibodies were assayed with an appropriate conjugate of anti-human IgG-HRP (1:100,000), 100 µL of it was coated in each well and kept at room temperature for 1 hour. Washing of the plate with TBS-T (five times) was followed by addition of 100 µL TMB in each well and incubation at room temperature for 5-20 min. The absorbance of each well was monitored at 450 nm on a VersaMax microplate reader (Molecular devices, Sunnyvale, Calif.).

What is claimed is:

1. A method of manufacturing a biopolymer optical waveguide comprising:
   providing a first biopolymer, wherein the biopolymer comprises a protein having a beta-sheet secondary structure; and
   casting said first biopolymer in a second polymer to form a biopolymer optical waveguide, the second polymer forming a polymer overcoat cladding proximate to the first biopolymer, wherein said first biopolymer and said second polymer have different indices of refraction.

2. The method of manufacturing the biopolymer optical waveguide of claim 1, wherein said providing of said first biopolymer includes unwinding said first biopolymer to extract individual biopolymer fibers.

3. The method of manufacturing the biopolymer optical waveguide of claim 2, further comprising tensioning said first biopolymer.

4. The method of manufacturing the biopolymer optical waveguide of claim 1, wherein said first biopolymer is silk.

5. The method of manufacturing the biopolymer optical waveguide of claim 4, wherein said second polymer is polydimethylsiloxane (PDMS).

6. The method of manufacturing the biopolymer optical waveguide of claim 1, wherein said first biopolymer has a higher index of refraction than said second polymer.

7. The method of manufacturing the biopolymer optical waveguide of claim 1, further comprising:
   treating the first biopolymer to remove surface roughness.

8. The method of manufacturing the biopolymer optical waveguide of claim 7, wherein said treating the first biopolymer to remove surface roughness is performed using laser ablation.

9. The method of manufacturing the biopolymer optical waveguide of claim 1, wherein said first biopolymer and said polymer overcoat form a concentric biopolymer waveguide along a longitudinal axis.

10. The method of manufacturing the biopolymer optical waveguide of claim 1, wherein said first biopolymer and said polymer overcoat form a rectangular slab waveguide along a planar axis.

11. The method of manufacturing the biopolymer optical waveguide of claim 1, wherein said first biopolymer comprises chitosan, collagen, gelatin, agarose, chitin, polyhydroxyalkanoates, pullan, starch (amylose amylopectin), cellulose, hyaluronic acid, or a combination thereof.

12. A method of manufacturing a biopolymer optical waveguide comprising:
   providing a substrate;
   printing a first biopolymer on said substrate, wherein the biopolymer comprises a protein having a beta-sheet secondary structure;
   depositing a second material on said first biopolymer to form said biopolymer optical waveguide, said second material having a lower index of refraction than said first biopolymer.

13. The method of manufacturing a biopolymer optical waveguide of claim 12, wherein said printing said first biopolymer on said substrate includes forming a layer of said first biopolymer, wherein said first biopolymer is a protein, and wherein said printing said first biopolymer is performed using an inkjet printer.

14. The method of manufacturing a biopolymer optical waveguide of claim 12, further comprising:
   overlay printing said first biopolymer to increase thickness of said biopolymer waveguide.

15. The method of manufacturing the biopolymer optical waveguide of claim 12, wherein said first biopolymer is silk.

16. The method of manufacturing the biopolymer optical waveguide of claim 15, wherein said second polymer is polydimethylsiloxane (PDMS).

17. The method of manufacturing the biopolymer optical waveguide of claim 12, further comprising:
   treating the first biopolymer to remove surface roughness.

18. The method of manufacturing the biopolymer optical waveguide of claim 17, wherein said treating the first biopolymer to remove surface roughness is performed using laser ablation.

19. The method of manufacturing the biopolymer optical waveguide of claim 12, wherein said first biopolymer comprises chitosan, collagen, gelatin, agarose, chitin, polyhydroxyalkanoates, pullan, starch (amylose amylopectin), cellulose, hyaluronic acid, or a combination thereof.

20. The method of manufacturing the biopolymer optical waveguide of claim 12, wherein said substrate is a template for an optical device.

21. The method of manufacturing the biopolymer optical waveguide of claim 20, wherein said substrate is a template for at least one of a lens, a microlens array, an optical grating, a pattern generator, and a beam reshaper.

22. A biopolymer optical waveguide comprising:
   a first biopolymer, wherein the biopolymer comprises a protein having a beta-sheet secondary structure; and
   a second material covering said first biopolymer to form said biopolymer optical waveguide, said second material having a lower index of refraction than said first biopolymer.

23. The biopolymer optical waveguide of claim 22, wherein said biopolymer optical waveguide is an in vivo diagnostic light delivery device.

24. The biopolymer optical waveguide of claim 23, wherein said in vivo diagnostic light delivery device is a light enabled nervous system replacement for damaged neurons.

25. The biopolymer optical waveguide of claim 22, wherein said biopolymer optical waveguide is a transmissive media for optical radiation that relays information from sensors.

26. The biopolymer optical waveguide of claim 25, wherein said transmissive media relays information from locations within a body.

27. The biopolymer optical waveguide of any one of claims 22-26, wherein the protein is silk fibroin.

* * * * *

UNITED STATES PATENT AND TRADEMARK OFFICE
CERTIFICATE OF CORRECTION

| | | |
|---|---|---|
| PATENT NO. | : 8,195,021 B2 | Page 1 of 1 |
| APPLICATION NO. | : 12/513387 | |
| DATED | : June 5, 2012 | |
| INVENTOR(S) | : Kaplan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 289 days.

Signed and Sealed this
Eleventh Day of September, 2012

David J. Kappos
*Director of the United States Patent and Trademark Office*